US009513237B2

(12) United States Patent
Brescello et al.

(10) Patent No.: US 9,513,237 B2
(45) Date of Patent: Dec. 6, 2016

(54) METHOD OF DETECTING POLYMORPHS USING SYNCHROTRON RADIATION

(75) Inventors: Roberto Brescello, Abano Terme (IT); Livius Cotarca, Cerignano Del Friuli (IT); Anna Smaniotto, Roncade (IT); Massimo Verzini, Caldiero (IT); Maurizio Polentarutti, Trieste (IT); Giorgio Bais, S. Vito Al Torre (IT); Jasper Rikkert Plaisier, Tricesimo (IT)

(73) Assignee: ZETACUBE S.R.L., Bresso (IT)

( * ) Notice: Subject to any disclaimer, the term of this patent is extended or adjusted under 35 U.S.C. 154(b) by 253 days.

(21) Appl. No.: 14/118,068

(22) PCT Filed: May 16, 2012

(86) PCT No.: PCT/EP2012/059127
§ 371 (c)(1),
(2), (4) Date: Jan. 24, 2014

(87) PCT Pub. No.: WO2012/156450
PCT Pub. Date: Nov. 22, 2012

(65) Prior Publication Data
US 2014/0185767 A1    Jul. 3, 2014

(30) Foreign Application Priority Data

May 17, 2011 (EP) ..................... 11166354

(51) Int. Cl.
*G01N 23/20*    (2006.01)
(52) U.S. Cl.
CPC ......... *G01N 23/20* (2013.01); *G01N 2223/203* (2013.01); *G01N 2223/652* (2013.01)

(58) Field of Classification Search
CPC .............. G01N 23/20; G01N 2223/203; G01N 2223/652

(Continued)

(56) References Cited

U.S. PATENT DOCUMENTS 5,353,236 A * 10/1994 Subbiah ................. G09B 23/26
700/266
7,263,162 B2 * 8/2007 Thorne ................... C30B 29/58
250/440.11

(Continued)

FOREIGN PATENT DOCUMENTS

WO    WO-01/82659 A1    11/2001
WO    WO-02/052919 A2    7/2002
WO    WO-2010/141063 A1    12/2010

OTHER PUBLICATIONS

Varasteh, et al ("Quantitative determination of polymorphic impurity by X-ray powder diffractometry in an OROS (R) formulation", Int'l J. Pharmaceutics, vol. 366, No. 1-2, Jan. 21, 2009, pp. 74-81, XP025839901).*

(Continued)

*Primary Examiner* — Michael Maskell
(74) *Attorney, Agent, or Firm* — Polsinelli PC

(57) ABSTRACT

A method of detecting polymorphs using X-ray produced by a synchrotron source is described. In particular, the method allows to detect particular polymorphs present in small amounts in mixtures of polymorphic compounds present in a prevailing amount. The method offers a powerful resolution of mixtures of polymorph and finds application particularly in the pharmaceutical field.

16 Claims, 8 Drawing Sheets

(58) Field of Classification Search
USPC .............................................. 378/71, 73, 75
See application file for complete search history.

(56) References Cited

U.S. PATENT DOCUMENTS

| | | | |
|---|---|---|---|
| 2002/0075995 A1* | 6/2002 | Fewster | G01N 23/20 378/81 |
| 2004/0209304 A1 | 10/2004 | Stahly et al. | |
| 2012/0190127 A1* | 7/2012 | Fraden | B01D 9/00 436/174 |

OTHER PUBLICATIONS

Varasteh et al., "Quantitative determination of polymorphic impurity by X-ray powder diffractometry in an OROS® formulation", International Journal of Pharmaceutics, vol. 366 No. 1-2, Jan. 21, 2009, pp. 74-81.

Cooper et al., "Quantification of crystalline forms in active pharmaceutical ingredient and tablets by X-ray powder diffraction", Journal of Pharmacy and Pharmacology, 2003, vol. 55. No. 9, Sep. 1, 2003, pp. 1323-1329.

Uvarov et al., "Development and metrological characterization of quantitative X-ray diffraction phase analysis for the mixtures of clopidogrel bisulphate polymorphs", Journal of Pharmaceutical and Biomedical Analysis, vol. 46, No. 4, 26 Nov. 2007, pp. 676-682.

Gregory A. Stephenson, "Applications of X-Ray Powder Diffraction in the Pharmaceutical Industry", The Rigaku Journal, vol. 22, No. 1, 2005, pp. 2-15.

Dong et al., "Application of X-ray scattering in pharmaceutical science", International Journal of Pharmaceutics, Jan. 21, 2011, pp. 1-11.

Nemet et al., "Quantifying low levels of polymorphic impurity in clopidogrel bisulphate by vibrational spectroscopy and chemometrics", Journal of Pharmaceutical and Biomedical Analysis, vol. 49, No. 1, Jan. 15, 2009, pp. 32-41.

Agatonovic-Kustrin et al., "Analysing the crystal purity of mebendazole raw material and its stability in a suspension formulation", International Journal of Pharmaceutics, vol. 361, No. 1-2, Sep. 1, 2008, pp. 245-250.

* cited by examiner

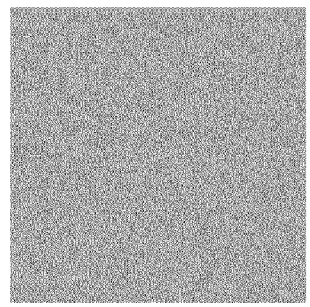
Fig. 4A
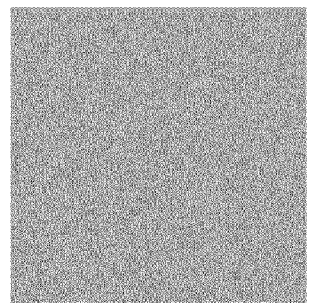
Fig. 4B
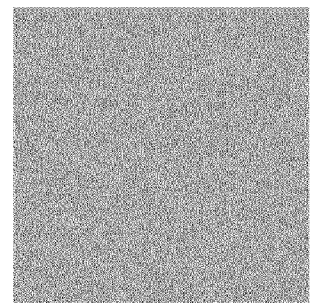
Fig. 4C
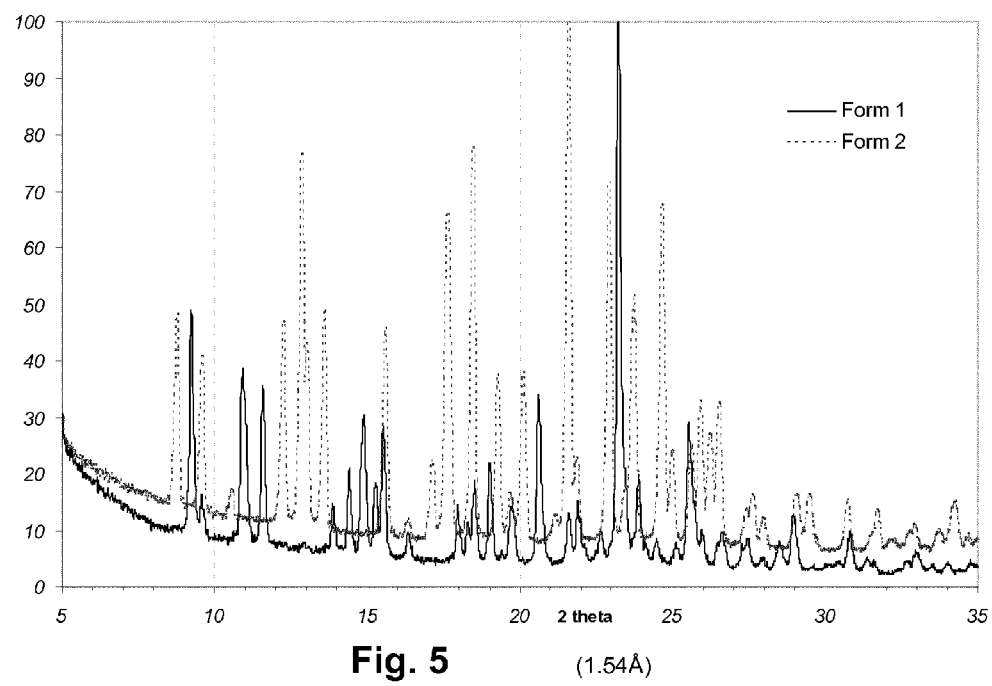
Fig. 5 (1.54Å)
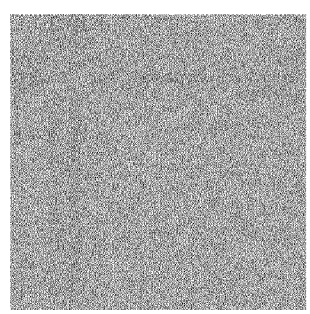
Fig. 6A
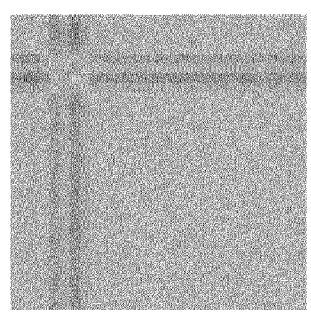
Fig. 6B
Fig. 6C

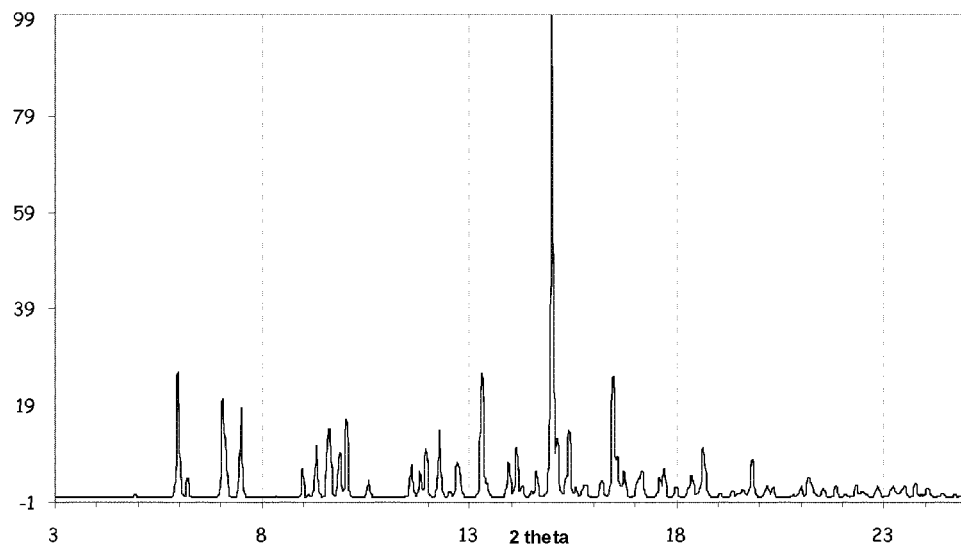
Fig. 7.a (1.0Å)
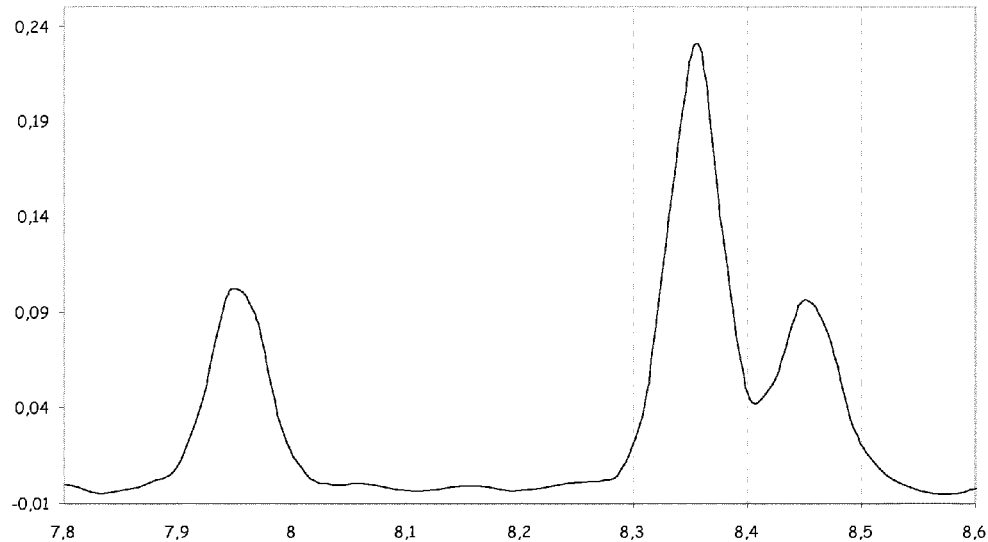
Fig. 7.b (zoom)

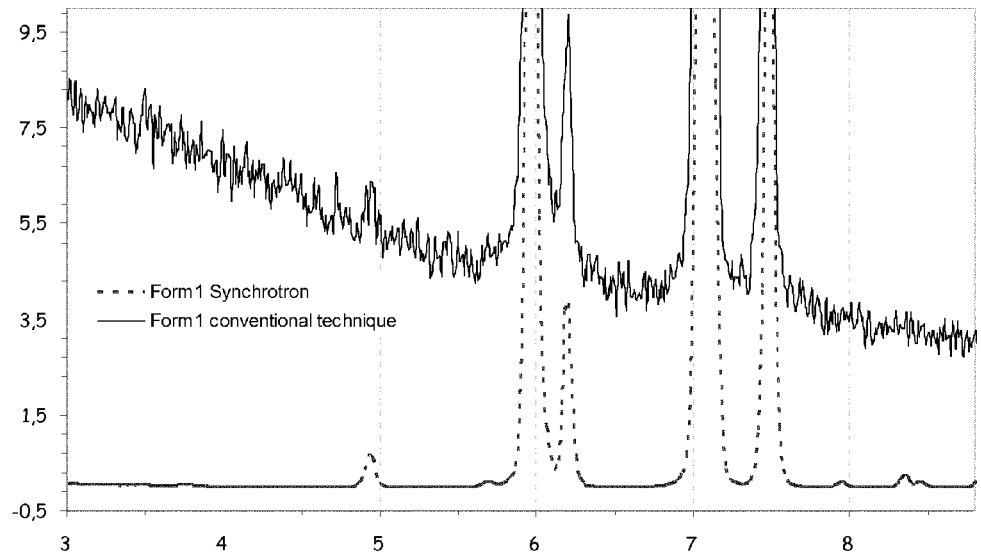
Fig. 8.a (1.0Å)
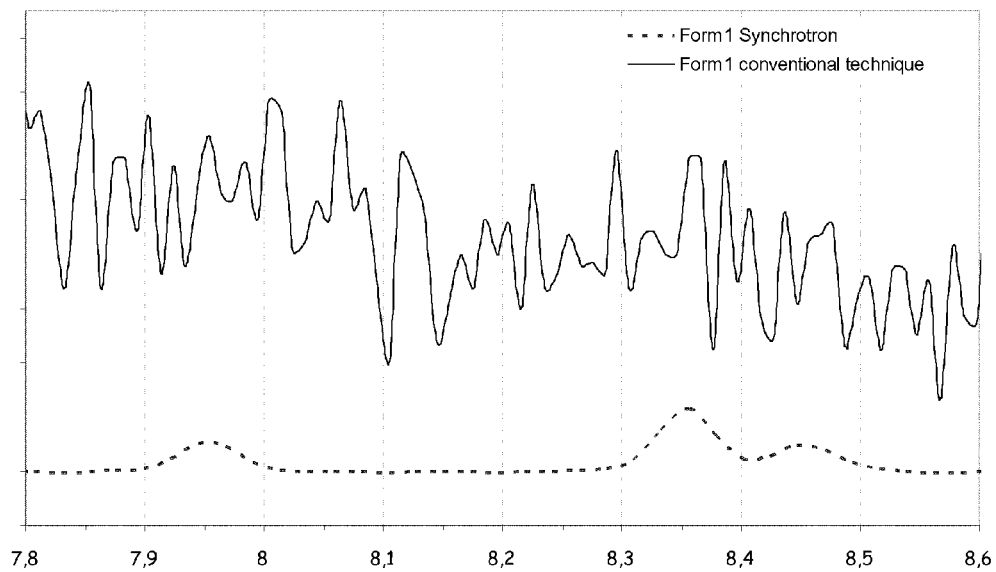
Fig. 8.b (zoom) (1.0Å)

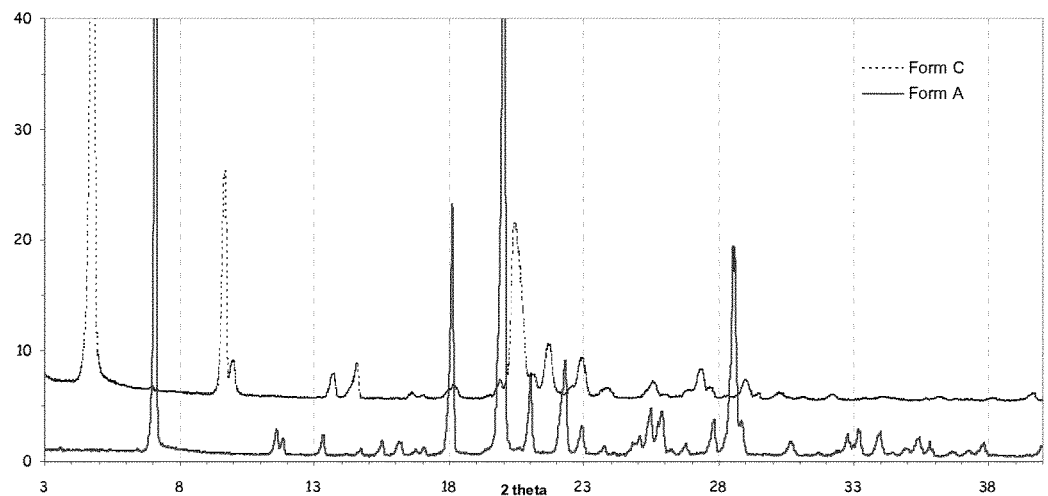
Fig. 9       (1.54Å)
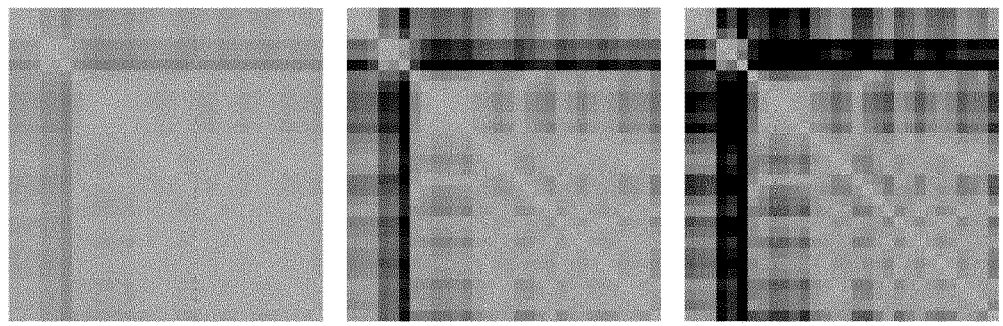
Fig. 10A            Fig. 10B            Fig. 10C

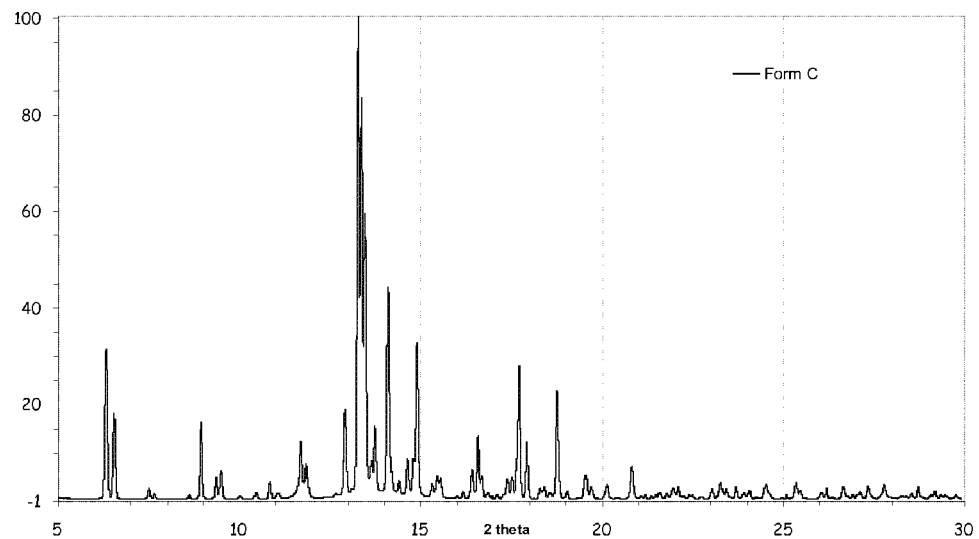
Fig. 11.a (1.0Å)
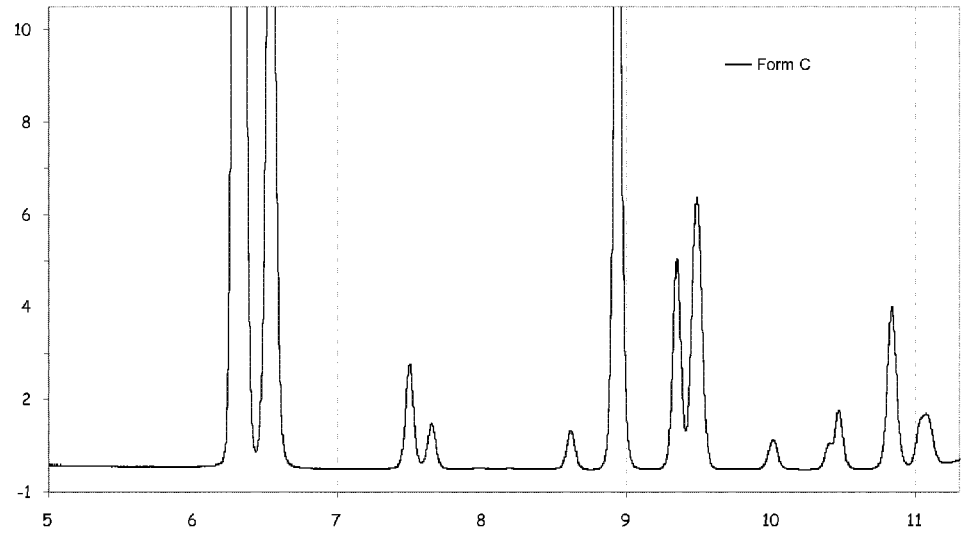
Fig. 11.b (zoom)

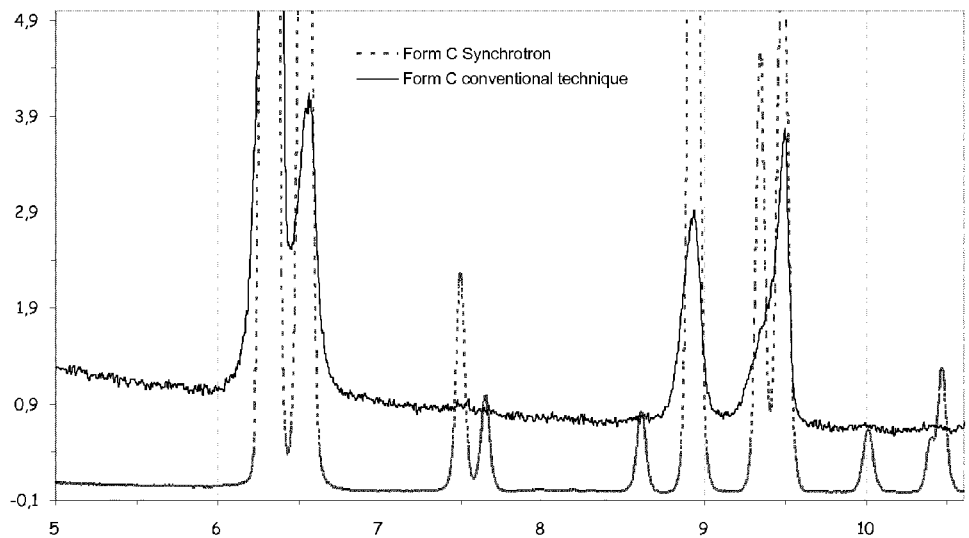
Fig. 12.a (1.0Å)
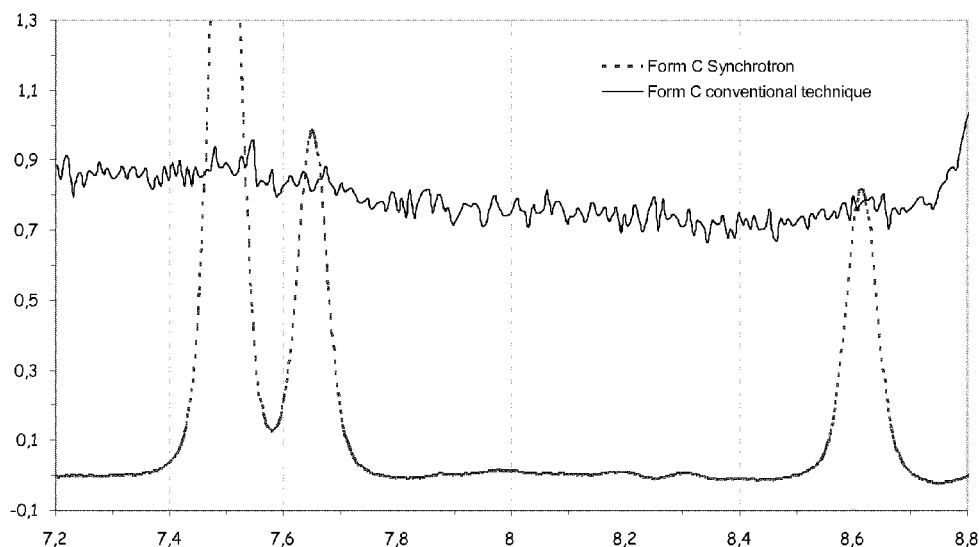
Fig. 12.b (zoom)

METHOD OF DETECTING POLYMORPHS USING SYNCHROTRON RADIATION

CROSS REFERENCE TO RELATED APPLICATIONS

This application is a National Phase filing under 35 U.S.C. §371 of PCT/EP2012/059127 filed on May 16, 2012; and this application claims priority to Application No. 11166354.8 filed in Europe on May 17, 2011, under 35 U.S.C. §119; the entire contents of all are hereby incorporated by reference.

Technical Field

The present invention relates to a method of detecting polymorphs using synchrotron radiation. In particular, the invention relates to a method of detecting particular polymorphs in mixtures of polymorphic compounds by using X-ray radiation from a synchrotron source. The invention relates also to an apparatus for carrying out such method.

The method of the invention finds application in different chemical fields and is particularly useful in the pharmaceutical field. It can be used with both active pharmaceutical ingredients (APIs) and formulated drug products such as tablets, suspensions, emulsions, creams, ointments and the like. The method can also be used in other fields where polymorphism and solvate-polymorphism is important, such as foods, pigments, cosmetics, agrochemicals, explosives, etc.

The term "active pharmaceutical ingredient" as used herein, is interchangeable with "drug substance".

A "polymorphic compound", or "polymorph", as used herein, means a compound having more than one solid form. For example, a polymorphic compound may have different forms of its crystalline structure, or different forms based upon hydration/solvation, or may have crystalline and amorphous forms. Amorphous solids consist of disordered arrangements of molecules and do not possess a distinguishable crystal lattice. Since only one polymorph is thermodynamically stable at a specified temperature and pressure, all the other polymorphs are potentially capable to be transformed into the stable polymorph. Some polymorph transformations are rapid and reversible, others are not.

Background Art

The form of a compound may have an impact on biological activity. The same chemical compound may exhibit different properties depending upon which form that compound is in (e.g. amorphous or crystalline). For example, different solid forms have different solubility. As a result, different solid forms, including different crystalline forms, of a chemical compound may have greater or lesser efficacy for a particular application. The identification of an optimal solid form is important in the pharmaceutical field, as well as in other fields such as foods, nutraceuticals, agrochemicals, pigments, explosives, etc.

In the pharmaceutical field it is important to find the form of a chemical compound that exhibits appropriate physical and chemical properties. One form may be more stable or have other properties that make it preferable over other forms. Desirable properties may be a better bioavailability, a better solubility, or better adsorption characteristics.

Manufacturing processes and/or purification processes are typically aimed at obtaining a chemical compound in the optimal polymorphic form. One or more polymorphs that do not exhibit the desired properties, however, can be formed.

Since a polymorphic form of a drug substance may be critical to the performance of a drug product, the different polymorphic forms may be categorized as impurities in a drug substance. Such polymorphic forms are thus regarded as contaminants of the desired drug substance.

Polymorphs of pharmaceutical solids can have different chemical and physical properties such as chemical reactivity, stability to air and light, apparent solubility, dissolution rate, optical and electrical properties. These properties can have a direct impact on the processability of drug substances and the quality/performance of drug products, such as stability, dissolution, and bioavailability and processing issues such as caking, static, bulk density compressability, tablet hardness and fracture.

Regulatory authorities may refuse to approve a generic drug referencing a listed drug if the application contains insufficient information to show that the drug substance is the "same" as that of the reference listed drug. A drug substance in a generic drug product is generally considered to be the same as the drug substance in the reference listed drug if it meets the same standards for identity. Because drug product performance depends on the product formulation, the drug substance in a proposed generic drug product needs not have the same physical form (particle size, shape, or polymorph form) as the drug substance in the reference listed drug. Since polymorphs may exhibit certain differences in physical and solid state chemistry (reactivity) attributes that relate to stability and bioavailability, however, it is essential that the product development and the regulatory review process pay close attention to this issue. This scrutiny is required to ensure that polymorphic differences (when present) are properly addressed via design and control of formulation and process conditions to ensure physical and chemical stability of the product over the intended shelf-life, as well as bioavailability/bioequivalence.

Development of methods to detect and/or determine the polymorph purity of a drug substance is thus an important task of the pharmaceutical industry.

U.S. Pat. No. 6,750,064 B2 discloses methods of screening for possible solid forms of a substance, particularly a pharmaceutical substance. Several analytical methods are discussed, including X-ray diffraction analysis.

X-ray diffraction patterns provide a powerful tool to analyze different crystalline forms or amorphous form of a substance. X-ray diffraction analysis is thus widely used to fingerprint polymorphs in a drug substance. The resolution and intensity of conventional X-ray sources, however, limit X-ray diffraction analysis and may not permit to identify and/or determine small amounts of a polymorph in a mixture, or to identify and/or determine the presence of a polymorph when its diffraction peaks overlap with the peaks of another polymorph, particularly if the latter is present in a larger amount.

Although powder X-ray diffraction is one of the most useful and widely used analytical methods to determine polymorphs and quantify the forms present in a mixture, detection limit determination becomes critical in the analysis of mixtures, particularly with respect to the sensitivity to detect small amounts of a given phase relative to another present in a larger amount. Small changes in the X-ray powder patterns due to the appearance of new peak(s), additional shoulders or shifts in the peak position often imply the presence of a new polymorph, but ambiguity in the data arises from insufficient resolution and sensitivity.

WO 01/82659 A1 discloses methods for the high throughput screening of polymorphs using a synchrotron X-ray source. The methods described in such a document are aimed at obtaining a large number of powder diffraction patterns from small quantities of material as part of an effort to fingerprint which polymorphic form a potential drug candidate has been produced by a particular synthetic procedure. In particular, the methods are designed to permit rapid rate at which data may be read from the detector, so that small sample sizes and short irradiation times may be utilized, permitting the high throughput analysis of thousands of samples per day. Owing to this, the diffraction data obtained need not be of a quality sufficient to solve the crystal structure of the sample compound.

Varasteh M. et al: "*Quantitative determination of polymorphic impurity by X-ray powder diffractometry in an OROS® formulation*", International Journal of Pharmaceutics, vol. 366 (2009) 74-81, discloses the determination of polymorphs A and B in an Alza Oros® drug delivery system by several analytical methods, including conventional X-ray Powder Diffractometry (XRD). The authors mentioned that a synchrotron radiation method has also been developed to quantify the crystallinity in substantially amorphous pharmaceuticals. Although such synchrotron radiation method is not discussed in detail, reportedly it is not directed to detect or determine polymorphs, and even less to detect/determine small amounts of polymorphs in products containing major amounts of another polymorph of the same compound.

Brett Cooper V. et al: "*Quantification of crystalline forms in active pharmaceutical ingredients and tablets by X-ray diffraction*", Journal of Pharmacy and Pharmacology, vol. 55, (2003); 1323-1329, discloses the characterization of polymorphs of an API under development by conventional XRD.

WO 02/052919 A2 discloses a method of searching for solid forms and screening a sample according to its form by using X-rays from a synchrotron source. The method is aimed at generating most possible solid forms of a compound for the purpose of screening and investigating such forms. To this purpose the method teaches to crystallize or solidify a compound from a sample in which the compound is not in solid form directly in a capillary or other receptacle suitable for X-ray analysis. The examples describe introducing solutions of the organic compound to be investigated in a capillary then evaporating the solvent so that several crystalline forms are formed. The method does not deal with the problem of detecting small amounts of polymorphs in products containing major amounts of another polymorph of the same compound.

There remain, thus, several disadvantages to, or problems not solved by, the methods disclosed in the cited references.

Moreover, none of these methods takes into consideration:
  (i) the possible effects of the radiation on the sample, which may damage the sample, cause a worsening of the quality of the data and change the polymorphic nature of the sample;
  (ii) how the form of the sample (e.g. powder, tablet, cream, suspension) determines/requires different measurement strategies in order to minimize the loss in resolution and/or accuracy due to the sample spatial extension and to maximize data quality;
  (iii) how the smaller beam divergence, intrinsic to synchrotron radiation and different from conventional sources, contributes to the data resolution and sensitivity, thus reducing the angular spread on the diffracted peaks, increasing the signal to noise ratio and reducing possible peaks overlapping.

SUMMARY OF DISCLOSURE

It has now been found that taking in account these factors is mandatory in order to ensure a correct detection of polymorphs present in small amounts or exhibiting X-ray diffraction patterns that overlap with other polymorphs present in a sample.

Therefore, the need is felt for a more sensitive method in detecting particular polymorphs in mixtures of polymorphic compounds.

Also, the need is felt for a more sensitive method in detecting particular polymorphs, which is efficient, reliable and commercially viable.

The present invention addresses this need by providing a method of detecting the presence and/or determining the amount of a non-prevailing polymorphic form of a polymorphic compound in the presence of one or more prevailing polymorphic forms, characterized by comprising the following steps:
  (A) providing a sample comprising said polymorphic compound in powder form or in a shaped solid form or in a form in which the solid polymorphic compound is suspended, dispersed or mixed with a liquid;
  (B) providing reference information from XRD analysis on the position of marker peaks of said non-prevailing polymorphic form of a said compound in a standard intensity versus scattering angle plot in relation to peaks of said one or more prevailing polymorphic forms;
  (C) providing a beam of a synchrotron radiation from a synchrotron source, said synchrotron radiation having a wavelength in the range from 0.5 to 3.0 Å;
  (D) exposing said sample to said beam with a spot size at said sample from $1\mu^2$ to $1\ cm^2$, said spot size being selected by using slits or pinholes;
  (E) checking the extent of possible damage caused by the exposure of the sample to the synchrotron radiation;
  (F) collecting the intensity and scattering direction of the diffracted radiation using a X-ray detector, while optionally rotating said sample; in order to probe different orientations of the sample volume hit by the beam;
  (G) moving one or more times said sample with respect to said beam to expose different areas of said sample to said beam and balance possible inhomogeneities of the sample, and repeating step (F) for said different areas of the sample;
  (H) processing the intensity and scattering direction data of said radiation collected by said detector to generate at least one plot reporting the scattered X-ray intensity versus scattering angle;
  (I) screening said plot to detect one or more marker peaks of said non-prevailing polymorphic form of said compound at scattering angles at which said one or more prevailing polymorphic forms do not have diffraction peaks; and
  (J) optionally processing the data corresponding to said one or more marker peaks to quantify said non-prevailing polymorphic form of said compound with respect to the prevailing form.

using different color shades to distinguish among different $cc_{xy}$ values of consistency.

FIG. 4A, FIG. 4B and FIG. 4C illustrate that no significant radiation damage was detectable.

FIG. 5 illustrates integrated diffraction patterns of reference compounds in Example 1.

FIG. 6A, FIG. 6B and FIG. 6C illustrate the consistency of data obtained exploiting Synchrotron radiation, which is highlighted by the gray boxes.

FIG. 7.a shows the diffractogram of a sample of a mixture containing Clopidogrel bisulfate Form 1 likely contaminated by Clopidogrel bisulfate Form 2, obtained with Synchrotron light at 1.0Å.

FIG. 7.b shows a zoom of a portion of FIG. 7.a with typical signals of Form 2.

FIG. 8.a and FIG. 8.b show the comparison between the same sample as above (mixture containing Clopidogrel bisulfate Form 1 likely contaminated by Clopidogrel bisulfate Form 2) analyzed with Synchrotron light and with a conventional technique. With the conventional technique it was not possible to see traces of Form 2, which were under the limit of detection, see FIG. 8.b.

FIG. 9 illustrates integrated diffraction patterns of reference compounds in Example 2.

FIG. 10A, FIG. 10B and FIG. 10C illustrate the consistency of data obtained exploiting Synchrotron radiation is highlighted as shown by the gray boxes in these Figures, showing some degree of inhomogeneity in the sample FIG. 11.a shows the diffractogram of a sample of a mixture containing Retigabine Form C likely contaminated by Retigabine Form A analyzed with Synchrotron light at 1.0Å.

FIG. 11.b shows a zoom of FIG. 11.a with typical signals of Form A.

FIG. 12.a and FIG. 12.b Show the comparison at 1.0Å between the same sample as above mixture containing Retigabine Form C likely contaminated by Retigabine Form A) analysed with Synchrotron light and with a conventional technique. With the conventional technique it was not possible to see traces of Form A, which were under the limit of detection, see FIG. 12.b.

Figure 13:
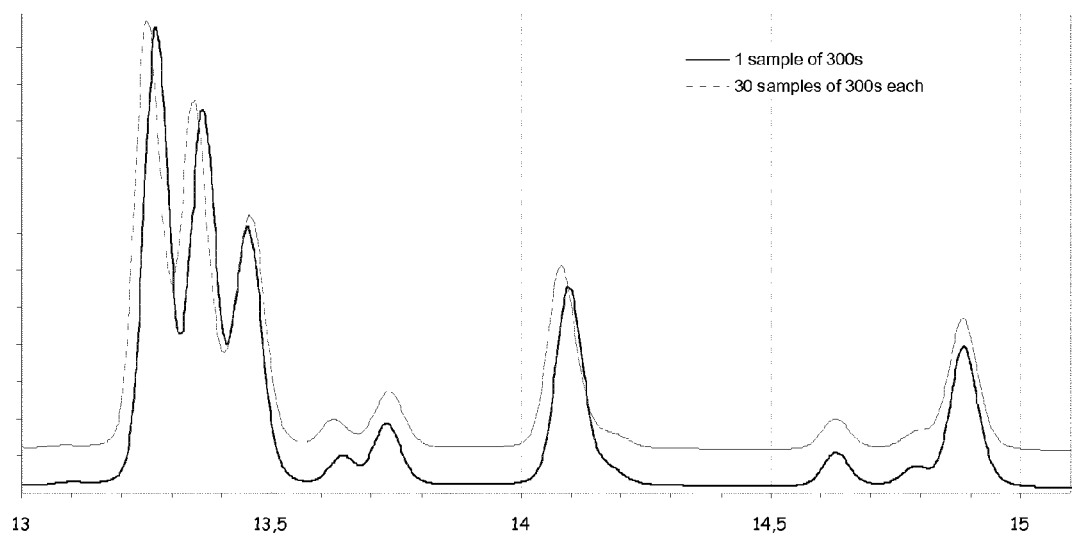

FIG. 13 shows the radiation damage caused by 30 consecutive exposures of 300s each, made on the same sample volume.

BEST AND VARIOUS MODES FOR CARRYING OUT DISCLOSURE

The method of the invention is particularly advantageous for detecting the presence and/or determining the amount of a non-prevailing polymorphic form of a polymorphic organic compound, more particularly a drug substance.

The method of the invention is directed in particular to the detection and/or determination of a polymorph in a mixture comprising other polymorphs and possibly other ingredients or components.

In the present description the term "detection of a polymorph" means identifying such polymorph from a qualitative point of view, while the term "determination of a polymorph" means quantifying the amount of such polymorph in a mixture or composition.

In the present description the term "non prevailing polymorphic form" or "non prevailing polymorph" means a polymorph that is present in a mixture or composition in an amount lower than the amount of a different polymorph, while the term "prevailing polymorphic form" or "prevailing polymorph" means a polymorph that is present in a mixture or composition in an amount higher than the amount of any other polymorph in the mixture or composition.

Although the present invention is not bound to a particular amount of a non prevailing polymorph in a mixture, the amount of a non prevailing polymorph in a mixture of polymorphs of a pharmaceutical product may be small or very small. For example it may be less than 5%, or less than 0.5%, or even less than 0.005% by weight.

The present invention addresses also the need of providing a method of detecting the absence of a non-prevailing polymorphic form of a polymorphic compound in the presence of one or more prevailing polymorphic forms.

In X-ray diffraction analysis of powders, signals observed from a small quantity of a pharmaceutical molecule are typically weak. An X-ray source extremely intense is required to increase the intensities of the signals and limit of detection.

Synchrotron radiation is generated when charged particles travel along curved trajectories at speeds close to that of light. The curvature is produced by magnetic fields. The speed of the particles and intensity of these fields determine the spectral distribution of the electromagnetic radiation produced. In general, a spectrum ranging from short-wavelength $\lambda$-rays, e.g. $<0.1 \times 10^{-10}$ m (=0.1 Å) up to the ultraviolet (e.g. 200 nm=2,000 Å) is available. In contrast to X-ray conventional sources, the synchrotron source offers higher radiated power (essential for samples containing small or very small amount of prevailing and non prevailing polymorphs), the possibility to select different specific wavelengths (essential to reduce sample absorption, sample fluorescence, diffraction background signal, sample damage), smaller divergences (essential to increase the signal to noise ratio and the resolution of neighbouring peaks) and well-defined state of polarization.

The method of the invention is based on X-ray diffraction analysis using synchrotron radiation and allows detection of very small amounts of polymorphs in a sample, even amounts at the level of impurities, such as 0.005%, as mentioned above.

The method of the invention can be carried out on a sample containing essentially only a compound comprising one or more polymorphic forms, or on a sample of a formulated product or composition, namely a sample containing a compound comprising one or more polymorphic forms and other ingredients or components.

The method of the invention can be carried out on a sample of loose powder or pressed powder or a shaped sample such as a tablet or the like, or in a formulation in which the solid polymorphic compound is suspended, dispersed or mixed with a liquid. Examples of such formulations are suspensions, emulsions, creams, gels, ointments and the like.

The method of the invention can also be carried out without removing the product to be analyzed from its packaging (e.g. a pharmaceutical product and its blister).

The method of the invention can be carried out on a sample that comprises also excipients and other ingredients (e.g. tablets of a pharmaceutical product).

The high energy of the radiation used requires an appropriate handling and/or treatment of the sample. Preliminary tests with synchrotron radiation to find out possible damages or alteration (e.g. decomposition, dehydration, polymorphic transition) of the sample due to the radiation are required.

An X-ray diffraction pattern plots the scattered X-ray intensity (I) as a function of diffraction angle (2θ). Because each crystalline material has a characteristic structure, it diffracts X-rays in a unique characteristic pattern. Therefore different crystalline structures exhibit different X-ray diffraction patterns, which fingerprint each structure. Marker peaks are present at given diffraction angles and are recorded and stored as reference data for each compound and/or polymorph.

As part of the preliminary steps to be carried out in the method of the invention, suitable reference X-ray diffraction patterns of the polymorph(s) to be investigated are collected and stored.

Also, proper functioning of the X-ray detection system is checked via wavelength calibration and calibration of spatial parameters that define the position of the detector with respect to the position of the sample to be analyzed. Standard reference systems are used for both calibrations.

Step (A) of the method according to the invention is that of providing a sample comprising the polymorphic compound to be analysed in powder form or in a shaped solid form or in a form in which the solid polymorphic compound is suspended, dispersed or mixed with a liquid. As disclosed above, "shaped form" means a form in which the sample has a sufficiently stable shape to be maintained in normal ambient conditions, such the shape of a tablet or capsule. If the sample is a powder, a suspension, emulsion, gel, cream, ointment, and the like, it can placed in a suitable capillary of quartz/Kapton/borosilicate (or similar appropriate materials) or other support/container of appropriate size for X-ray analysis. Milled or micronized samples can be also used. If the sample is a shaped sample, e.g. a tablet, it is used as such. As mentioned above, the sample can be left in the package or blister that contains it. In this case a X-ray diffraction pattern of the blister only—or other similar container—is collected in similar experimental conditions and used as reference for the analysis of the sample.

Since the method is designed to detect the presence or absence of a small amount of a polymorph in a sample containing a large amount of another polymorph, the sample to be analysed is typically a compound or a mixture in which a desired polymorphic compound may be associated to a smaller amount of an undesired polymorph. This may occur for instance if the production process of the desired polymorphic compound (the "prevailing polymorphic form") yields as a by-product or impurity an undesired polymorphic compound (the "non prevailing polymorphic form").

Step (B) of the method is that of providing reference information from XRD analysis on the position of marker peaks of the non-prevailing polymorphic form of a compound in a intensity versus scattering angle plot in relation to peaks of one or more prevailing polymorphic forms. This means that X-ray diffraction patterns of each polymorphs or ingredients to be investigated are available as reference data and are provided to the analyst that carries out the method, or to an automated system that is programmed to carry out the method.

Step (C) of the method is that of providing a beam of a synchrotron radiation from a synchrotron source. An X-ray beam from a synchrotron source with a wavelength in the range from 0.5 to 3.0 Å is selected taking into consideration maximum brilliance, sample absorption, radiation damage, sample fluorescence. Preferably said synchrotron radiation has a wavelength in the range from 0.8 to 1.5 Å.

Although synchrotron radiation is not as readily available as a conventional X-ray source, several synchrotron radiation sources are available in Europe, the United States and other countries with advanced R&D facilities.

Step (D) of the method comprises exposing the sample to be analysed to the beam of synchrotron radiation with a spot size at the sample from $1\mu^2$ to 1 cm$^2$, said spot size being selected by using slits or pinholes. Preferably the spot size at the sample is from $100\mu^2$ to 0.1 cm$^2$.

In the following description the step of exposing the sample to the beam of X-ray is called "measure" or "measurement" or "sampling", although strictly speaking the measure includes also the collection of the data and their processing up to a final diffraction pattern. The samples to be analysed are typically exposed to a synchrotron radiation having preferably a wavelength in the range 0.8 to 1.5 Å and preferably a spot size at the sample variable from 200 μm to 300 μm in diameter, in order to assess the diffractive power of the sample and select appropriate collection parameters.

Parameters to be selected include, but are not limited to:
desired minimum and maximum angular resolution;
exposure time, in order to not exceed the dynamic range of the detector but still obtain sufficient signals from the diffraction peaks, including weaker peaks;
size of the beam, so that as much sample as possible is measured and the intensity of diffraction peaks is increased, taking into account the broadening of diffraction peaks due to over-extended samples;
wavelength used, so that the absorption of X-rays in the sample is minimized and the diffraction with the sample is maximized. The choice of the wavelength should also minimize and possibly delete any contribution from the possible fluorescence from the sample since it may reduce the quality of data obtained. It also affects the desired minimum and maximum resolution, as well as the distance between detector and sample. Moreover the wavelength choice determines the level of scattering background and therefore the quality of the data.
Sample-detector distance. This must mainly ensure the possibility that the diffraction peaks are resolved. The variation of this parameter also affects the minimum and maximum angular resolution.
Position of the beamstopper, so that the shadow produced by the beamstopper on the detector is minimized in order to improve the minimum scattering angle of the data collected, as well as to minimize the background recorded by the detector due to the interaction of X-rays and air. An optimal position of the beamstopper improves the signal-to-noise ratio of the data.

Step (E) of the method comprises checking the extent of the possible damage caused by the exposure of the sample to the synchrotron radiation; the selected area on the sample is exposed for different time intervals to the X-ray beam. The time intervals are chosen as fractions of the selected exposure time (step D) in order to monitor possible radiation damages during a single measurement with the selected parameters. Longer intervals are also monitored in order to highlight possible radiation damage after prolonged exposures. During these time intervals X-ray diffraction patterns are recorded and the correlation among them is used to evaluate the amount of radiation damage. This provides an estimated maximum exposure time without damage. If necessary the chosen exposure time (step D) is changed accordingly.

When the optimal parameters are selected, they are kept constant during the performance of the method so that any variation that could affect the comparability of the data is avoided.

Step (F) of the method comprises collecting the intensity and scattering direction of the diffracted radiation using a X-ray detector directing the X ray beam having the selected characteristics onto the sample. During the measurement, the sample may be moved about one or more axis with respect to the X-ray beam to balance possible inhomogeneities in the crystallites orientation in the sample volume hit by the beam. The extent and degree of such motion (in general a rotation, see FIG. 1 as example on a capillary) during the X-ray exposure is assessed and selected.

Scattered (or diffracted) radiation is recorded with an area X-ray detector. The resulting image obtained through the detector consists of a matrix whose size depends on the type and model of detector, in which each element of the matrix records a value related to the amount of X-ray diffracted in a certain direction of the space. The values of the matrix are contained in an appropriate file format, typically a suitable image to be displayed by a computer system.

Optionally a point or line detector may be used to obtain the diffraction intensities and scattering directions.

Step (G) of the method comprises moving one or more times the sample to be analysed with respect to the beam of synchrotron radiation. This allows exposing different areas of the sample to the radiation and balance possible inhomogeneities of the sample. Several measures are thus performed for each sample, in a manual or automated way, in different parts of the sample in order to improve the statistics of the data. Such measures are generally performed in a capillary tube if the sample is a loose crystalline powder or in a form in which the solid polymorphic compound is suspended, dispersed or mixed with a liquid. The measures are performed directly on the sample if this is in a "shaped form" as defined before (e.g. tablet). The total number of measurements collected on a sample is such to match an established statistical confidence. Usually at least 10 measurements are performed on each sample.

The amount of tested sample as a whole depends on the number of measurements, the size of the beam and the packing density of the sample in the sample holder, for example a capillary tube or simply a tablet holder.

Figure 1:
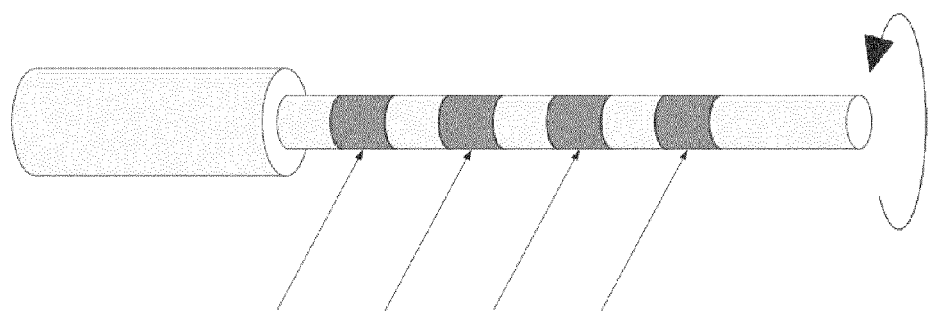
FIG. 1 illustrates rotation of samples contained in a capillary during X-ray exposure.
Figure 2:
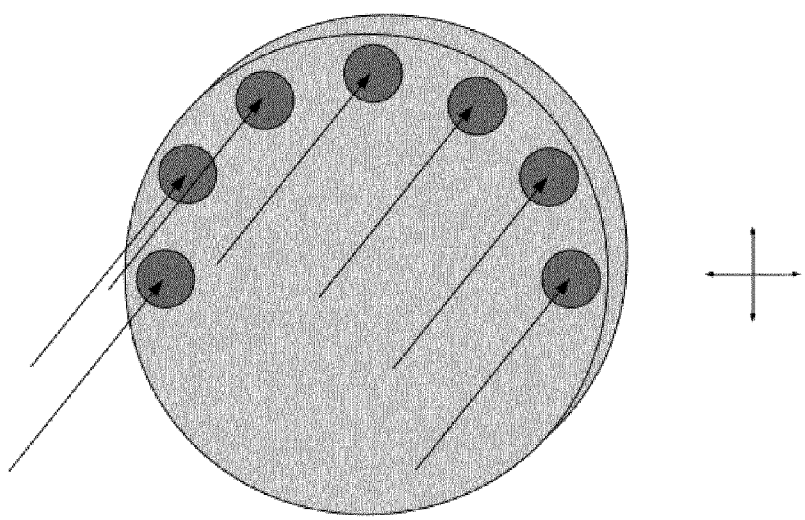
FIG. 2 illustrates that in the case of tablets of circular section measurement is typically made in the vicinity of the maximum circumference.

In the case of samples contained in a capillary, this is held in rotation during exposure to X-rays, usually along its main axis, as shown in FIG. 1 and described in step (F). In such case the measurements, described in step (G), take place along the length of the axis. Conversely, in the case of formulations or tablets, since the spatial extension of the sample would produce a broadening of the diffraction peaks, and then a worsening of the quality of the final pattern, the measurement is made where the thickness of the sample is smaller. In the case of tablets of circular section the measure is thus typically made in the vicinity of the maximum circumference, as shown in FIG. 2, making sure, however, to sample also the inner part of the tablet, for a comparison of the data.

Step (H) of the method comprises processing the data of the radiation collected by the detector to generate at least one intensity versus scattering angle plot.

The images representing the intensity of the X-rays diffracted from the sample may appear in different ways depending on the degree of crystallinity of the sample and its diffractive power. Where the sample is a crystalline powder or a crystalline powder mixed with an amorphous material, the appearance of the image is generally that of an array of concentric rings more or less uniform, depending on the size of the individual crystals that make up the powder. Radial profile shows peaks superimposed on a background of different shape, due to the amorphous component of the sample, which produces no diffraction peaks, and to the interaction of the X-rays with the sample holder (e.g. the capillary) and the molecules present in the air between the sample and the detector.

The symmetry of the diffraction pattern allows for a circular integration of the peaks, with the following result:
improvement of the signal to noise ratio for each peak;
elimination/reduction of inhomogeneity along each circumference due to preferred orientations of individual crystals.

The integration above is performed by using suitable programs (e.g. Fit2d, AreaDiffractionMachine) whose key parameters are distance, wavelength, position and orientation (angular) of the detector compared to the sample and incoming X-ray beam, as obtained from preliminary measurements on reference samples.

The result of the integration is thus a function that plots a radial distance from the centre of symmetry of the initial images (expressed as an angle 2θ) vs. the height of the signal, namely the intensity.

To make easier a comparison of data with those obtained with conventional sources, also the horizontal axis on the position of angular peaks is rescaled due to the different wavelengths used (λ) following Bragg's law.

In the present description the terms "intensity versus scattering angle plot" and "integrated diffraction pattern" are used interchangeably.

The information contained in the integrated diffraction pattern is enhanced by taking into consideration the contribution of the air and the contribution of the sample holder (e.g. capillary). This is achieved by acquiring one or more images of an empty capillary while keeping unchanged the remaining parameters. It is thus possible to obtain images to be integrated as before, and to be subtracted from the previous images, so that these latter are representative of the sample only, namely of its crystalline component (which produces peaks) and of its amorphous component (which produces a background line).

A background line can also be obtained using mathematical or empirical methods.

The quality of the data obtained for the diffraction peaks (e.g. their positions and their intensity) may be enhanced by performing several measurements, as said above, thus obtaining several diffraction patterns. The quality of the data is then assessed by performing—after integration and subtraction of the background—a comparison of each pattern with the others. A quantification of the degree of repeatability, namely of the consistency, of the measurements is made by calculating the degree of correlation (cc) between each pair of patterns. The following relation is used, where x and y represent each pair of diffraction patterns:

$$cc_{xy} = \Sigma xy / \sqrt{\Sigma x^2 \cdot \Sigma y^2}$$

Figures 3A, 3B, 3C:
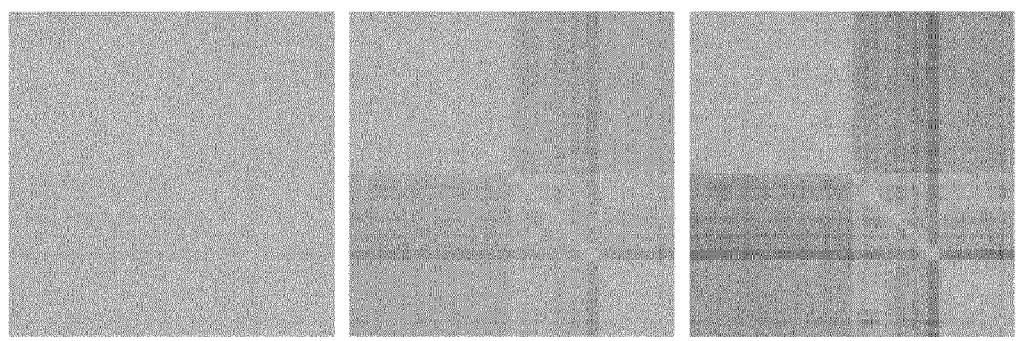
FIG. 3A, FIG. 3B and FIG. 3C are graphical representation of $cc_{xy}$ values of the equation $$cc_{xy} = \Sigma xy / \sqrt{\Sigma x^2 \cdot \Sigma y^2},$$

The relation above provides, for each pair of patterns, a value of degree of correlation comprised between 0 (completely unrelated measurements) and 1 (perfectly repeatable measurements). Owing to the large number of coefficients to be assessed, a graphical representation of such coefficients is used. In such representation a color (e.g. gray) is associated to each $cc_{xy}$ value, using different color shades to distinguish among different $cc_{xy}$ values. The values of the correlation are then placed in a matrix whose entries are the patterns under investigation. In the matrices (gray boxes) the value of consistency and represented by a scale of gray: the white color represents the highest correlation, namely $cc_{xy}=1$; a black color represents a minimum of consistency, generally 0.5 (FIG. 3A), 0.9 (FIG. 3B) or 0.95 (FIG. 3C).

The matrices are used to reveal possible inhomogeneities in spatial distribution of the different polymorphic forms in the sample, possible inhomogeneities of the packing of the sample, highlight technical failures during the data collection and different degrees of crystallinity of the polymorphs in the sample.

This information can lead to the exclusion of some data from the dataset, exclude the whole sample because non representative or on the other hand confirm the quality of the collected data. Matrices can be used on the data relative to crystalline component of the sample as well as to its amorphous component as well as to both, giving similar and complementary information on the homogeneity of the sample and its statistical representativeness.

Step (I) of the method comprises screening the plot obtained at step (H) to detect one or more marker peaks of the non-prevailing polymorphic form of the polymorphic compound to be investigated at scattering angles at which said one or more prevailing polymorphic forms do not exhibit diffraction peaks.

After having checked the good consistency of the data (step H), it is possible to screen and compare the positions of the diffraction peaks with the positions of peaks obtained from reference compounds, or from the literature or available reference databases. Such comparison is thus carried out on the basis of reference X-ray patterns of the prevailing polymorphic compound and on the basis of reference X-ray patterns of the non-prevailing polymorphic compound that is to be detected.

Since the prevailing polymorphic compound may have peaks at scattering angles at which also the non-prevailing polymorphic compound has peaks that could overlap with—and be masked by—the prevailing polymorphic compound, the screening and comparison is made at scattering angles at which the prevailing polymorphic compound does not have diffraction peaks but the non-prevailing polymorphic compound does have diffraction peaks.

By this comparison peaks that characterize the non-prevailing polymorphic form of the compound under investigation are detected or—with a given confidence level—their absence is confirmed. The higher sensitivity (limit of detection) ensured by the synchrotron radiation makes it possible to detect marker peaks of very small amounts of one or more polymorphs of the compound under investigation, which would not be possible by using conventional X-ray source.

Step (J) of the method is optional and relates to the quantitative determination of the non-prevailing polymorphic form(s) of the compound contained in the sample.

Once one or more peaks characterizing a polymorphic form are detected, a quantitative determination of the content of that polymorphic form in the sample is possible. The procedure comprises using the signal of a marker peak in at least two samples with a known content of polymorphs, calculated as areas of the marker peaks once normalized to the strongest peak to the prevailing polymorphic form. As a next step a calibration curve is defined by using the signals corresponding to the known amounts of polymorph, then this calibration curve is used to determine the polymorph content of the samples under investigation. An experimental error is associated to such calibration curve starting from the error associated to the polymorphic content of the known samples.

The analysis of the X-ray diffraction pattern according to the method of the present invention allows to identify the crystalline and amorphous components of the sample. More particularly it allows:

to estimate the quantitative ratio between the two components by comparing the areas under the diffraction peaks with the area under the background;

to analyze the crystalline component and detect the position and relative intensities of the diffraction peaks, including to detect marker peaks of different polymorphs present in the sample.

EXAMPLES

The following examples illustrate the method of the invention.

Example 1

Clopidogrel bisulfate is an oral, thienopyridine class anti-platelet agent used to inhibit blood clots in coronary artery disease, peripheral vascular disease, and cerebro-vascular disease. Clopidogrel bisulfate has a prevailing polymorph designated as Form 1 and one, non-prevailing, polymorph designated as Form 2.

A beamline of synchrotron apparatus located in Trieste, Italy, was used. The analytical system had the following optimized parameters:

x-ray wavelength: 1.0 Å;
Sample-detector distance: 400 mm;
x-ray spot size on sample: 200 μm×200 μm;
Detector: Pilatus (Dectris) 2M (254×289 mm$^2$, 0.172× 0.172 mm$^2$ pixel size).
Sample holder rotating capillary, 30 samples per capillary, 2 capillaries.
Sample rotation speed 1.2 degrees/sec, 300 seconds per exposure
data were integrated using fit2D;
No evidence of significant radiation damage was detectable using the above parameters, as shown by the gray boxes reported in FIG. 4.

For conventional X-ray technique analysis a Bruker D8 Advance instrument endowed with Bragg-Brentano geometry was used. The working conditions were:

x-ray tube: copper;
radiation K($\alpha$1) and K($\alpha$2), 1.54060 Å e 1.54439 Å;
tension and current of the generator: 35 kV, 50 mA;
LynxEye PSD detector, PSD window 0.8°;
step size: 0.016°;
time per step: 0.5 s;
2θ range: 3-40°;
sample holder with rotation.

Integrated diffraction patterns of reference compounds are shown in FIG. 5. The diffractograms were obtained by conventional technique with Copper anode.

The consistency of data obtained exploiting Synchrotron radiation is highlighted by the gray boxes of FIGS. 6A, 6B and 6C.

FIG. 7.*a* shows the diffractogram of a sample of a mixture containing Clopidogrel bisulfate Form 1 likely contaminated by Clopidogrel bisulfate Form 2, obtained with Synchrotron light at 1.0 Å. FIG. 7.*b* shows a zoom of a portion of previous FIG. 7.*a* with typical signals of Form 2. In FIG. 8.*a* is shown the comparison between the same sample as above analyzed with Synchrotron light and with conventional technique. With conventional technique it was not possible to see traces of Form 2, which were under the limit of detection, see FIG. 8.*b*.

Samples of the initial tests showed that the use of synchrotron radiation makes the technique far more sensitive than with conventional X-ray source, allowing the detection of impurities in very low percentage, which was not detectable through conventional sources.

Example 2

Retigabine is an anticonvulsant used as in the treatment of partial epilepsies. Retigabine has a prevailing polymorph designated as Form C and one, non-prevailing, polymorph designated as Form A.

A beamline of synchrotron apparatus located in Trieste, Italy, was used. The analytical system was the same as in Example 1.

For conventional X-ray technique analysis a Bruker D8 Advance instrument endowed with Bragg-Brentano geometry was used. The working conditions were:
x-ray tube: copper;
radiation K($\alpha$1) and K($\alpha$2), 1.54060 Å e 1.54439 Å;
tension and current of the generator 35 kV, 50 mA;
LynxEye PSD detector, PSD window 0.8°;
step size: 0.010°;
time per step: 2 s;
2$\theta$ range: 3-40°;
sample holder with rotation.

Integrated diffraction patterns of reference compounds are shown in FIG. 9. The diffractograms were obtained by conventional technique with Copper anode (1.54 Å).

The consistency of data obtained exploiting Synchrotron radiation is highlighted by the gray boxes of FIGS. 10A, 10B and 10C, showing some degree of inhomogeneity in the sample In FIG. 11.a it is reported a sample of a mixture containing Retigabine Form C likely contaminated by Retigabine Form A analyzed with Synchrotron light at 1.0 Å, and in FIG. 11.b it is shown a zoom of previous FIG. 11.a with typical signals of Form A. In FIG. 12.a it is shown the comparison at 1.0 Å between the same sample as above analysed with Synchrotron light and with conventional technique. With conventional technique it was not possible to see traces of Form A, which were under the limit of detection, see FIG. 12.b.

In FIG. 13 is shown the radiation damage caused by 30 consecutive exposures of 300 s each, made on the same sample volume. Due to radiation damage, the diffractogram shows some peak shifts, (for example at 14.1°), and some changes in peaks relative intensities. In order to avoid damages on Retigabine samples, exposure time was limited to 180 seconds for each measurement.

The invention claimed is:

1. A method of detecting the presence and/or determining the amount of a non-prevailing polymorphic form of a polymorphic compound in the presence of one or more prevailing polymorphic forms, comprising the following steps:
(A) providing a sample comprising said polymorphic compound in powder form or in a shaped solid form or in a form in which the solid polymorphic compound is suspended, dispersed or mixed with a liquid;
(B) providing reference information from XRD analysis on the position of marker peaks of said non-prevailing polymorphic form of a said compound in a standard intensity versus scattering angle plot in relation to peaks of said one or more prevailing polymorphic forms;
(C) providing a beam of a synchrotron radiation from a synchrotron source, said synchrotron radiation having a wavelength in the range from 0.5 to 3.0 Å;
(D) exposing said sample to said beam with a spot size at said sample from 100 $\mu^2$ to 0.1 cm$^2$, said spot size being selected by using slits or pinholes;
(E) checking the extent of possible damage caused by the exposure of the sample to the synchrotron radiation;
(F) collecting the intensity and scattering direction of the diffracted radiation using a X-ray detector, while optionally rotating said sample in order to probe different orientations of the sample volume hit by the beam;
(G) moving one or more times said sample with respect to the said beam to expose different areas of said sample to said beam and balance possible inhomogeneities of the sample, and repeating step (F) for different areas of the sample;
(H) Processing the intensity and scattered direction data of said radiation collected by said detector to generate at least one plot reporting the scattered X-ray intensity versus scattering angle;
(I) screening said plot to detect one or more marker peaks of said non-prevailing polymorphic form of said compound at scattering angles at which said one or more prevailing polymorphic forms do not have diffraction peaks.

2. The method according to claim 1, wherein said synchrotron radiation has a wavelength in the range from 0.8 to 1.5 Å.

3. The method according to claim 1, wherein said synchrotron radiation has a spot size at the sample from 200 to 300 $\mu$m.

4. The method according to claim 1, wherein said sample is in powder form or in a form in which the solid polymorphic compound is suspended, dispersed or mixed with a liquid and is contained in capillary tube supported by a sample holder which is rotated about the longitudinally axis of said capillary tube, to expose different areas of said sample to said radiation, whereby possible inhomogeneity of said sample is balanced.

5. The method according to claim 1, wherein said sample is in a form of a tablet and said different areas of the sample that are exposed to said beam of synchrotron radiation according to step (G) correspond to portions of said sample in which the thickness of the sample is smaller.

6. The method according to claim 1, wherein said step (H) comprises:
a. generating a plurality of intensity versus scattering angle plots;
b. performing a comparison of each plot with the others;
c. quantifying the degree of repeatability of the measurements by calculating a degree of correlation (cc) between each pair of plots according to the following relation $$cc_{xy} = \Sigma xy / \sqrt{\Sigma x^2 \cdot \Sigma y^2}$$

wherein x and y represent each pair of plot; said relation providing for each pair of patterns a value of degree of correlation comprised between 0 and 1.

7. The method according to claim 1, wherein said step (H) comprises: generating a plurality of intensity versus scattering angle plots; and wherein said step (I) comprises screening said plots having a degree of consistency of the measurements by calculating a degree of correlation (cc) between each pair of plots according to the following relation $$cc_{xy} = \Sigma xy / \sqrt{\Sigma x^2 \cdot \Sigma y^2}$$

wherein x and y represent each pair of plot; said relation providing for each pair of patterns a value of degree of correlation comprised between 0 and 1.

8. The method according to claim 2, wherein said sample is in powder form or in a form in which the solid polymorphic compound is suspended, dispersed or mixed with a liquid and is contained in capillary tube supported by a sample holder which is rotated about the longitudinally axis of said capillary tube, to expose different areas of said sample to said radiation, whereby possible inhomogeneity of said sample is balanced.

9. The method according to claim 3, wherein said sample is in powder form or in a form in which the solid polymorphic compound is suspended, dispersed or mixed with a liquid and is contained in capillary tube supported by a sample holder which is rotated about the longitudinally axis of said capillary tube, to expose different areas of said sample to said radiation, whereby possible inhomogeneity of said sample is balanced.

10. The method according to claim 2, wherein said sample is in a form of a tablet and said different areas of the sample that are exposed to said beam of synchrotron radiation according to step (G) correspond to portions of said sample in which the thickness of the sample is smaller.

11. The method according to claim 3, wherein said sample is in a form of a tablet and said different areas of the sample that are exposed to said beam of synchrotron radiation according to step (G) correspond to portions of said sample in which the thickness of the sample is smaller.

12. The method according to claim 4, wherein said sample is in a form of a tablet and said different areas of the sample that are exposed to said beam of synchrotron radiation according to step (G) correspond to portions of said sample in which the thickness of the sample is smaller.

13. The method according to claim 7, wherein said synchrotron radiation has a wavelength in the range from 0.8 to 1.5 Å.

14. The method according to claim 1, wherein further comprises a step (J) of processing the data corresponding to said one or more marker peaks to quantify said non-prevailing polymorphic form of said compound with respect to the prevailing form.

15. The method according to claim 14, wherein said step (J) comprises using the signal of a marker peak in at least two samples with a known relationship of content of polymorphs, calculated as areas of the marker peaks, and defining a related calibration line to determine the polymorph content of a samples with an unknown content of said polymorph.

16. The method according to claim 14, wherein said sample is in a form of a tablet and said different areas of the sample that are exposed to said beam of synchrotron radiation according to step (G) correspond to portions of said sample in which the thickness of the sample is smaller.

* * * * *